United States Patent

Rauch et al.

[11] Patent Number: 5,584,863
[45] Date of Patent: Dec. 17, 1996

[54] PULSED RADIO FREQUENCY ELECTROTHERAPEUTIC SYSTEM

[75] Inventors: Thomas Rauch, Conyers, Ga.; Arthur A. Pilla, Ridgewood, N.J.; Se Y. Oh, Deerfield Beach, Fla.

[73] Assignee: Electropharmacology, Inc., Pompano Beach, Fla.

[21] Appl. No.: 501,290

[22] Filed: Jul. 12, 1995

Related U.S. Application Data

[63] Continuation of Ser. No. 291,843, Aug. 17, 1994, abandoned, which is a continuation-in-part of Ser. No. 257,281, Jun. 9, 1994, abandoned, which is a continuation-in-part of Ser. No. 82,610, Jun. 24, 1993, abandoned.

[51] Int. Cl.⁶ .................................................. A61N 1/40
[52] U.S. Cl. ............................................ 607/2; 607/71
[58] Field of Search ................................ 607/2, 71, 155

[56] References Cited

U.S. PATENT DOCUMENTS

| | | | |
|---|---|---|---|
| 2,276,996 | 3/1942 | Milinowski | 607/101 |
| 3,270,746 | 9/1966 | Kendall et al. | 607/155 |
| 3,800,802 | 4/1974 | Berry et al. | 607/71 |
| 4,305,115 | 12/1981 | Armitage | 607/154 |

*Primary Examiner*—William E. Kamm
*Attorney, Agent, or Firm*—Hopgood, Calimafde, Kalil & Judlowe

[57] ABSTRACT

A system for tissue-impedance matched pulsed radio frequency (PRF) electrotherapy includes a power supply, an excitation board for generating PRF signals of a selectable frequency, the board having an input from the power supply. The system also includes a power amplifier for signals from the excitation board. Included is a subsystem for controlling pulse width duration, pulse burst repetition rate, and amplitude of the PRF signals, the controlling system having an input from the power supply. Further provided is a subsystem for continually comparing the amplitude of the PRF signals outputted from the amplifier to a reference value, this including a feedback circuit responsive to difference information between the compared signals and the reference value, the difference information inputted to the controlling subsystem for adjustment of the amplitude and impedance of the PRF signals from the excitation board, the comparing system including an output of power and impedance compensated PRF signals. The system also includes a variable reactance athermapeutic applicator having, as a coaxial cable input, the power and impedance compensated PRF signals outputted from the comparing subassembly, the applicator including a treatment surface having an effective physiologic impedance in the range of 25 to 75 ohms.

11 Claims, 8 Drawing Sheets

PULSED RADIO FREQUENCY ELECTROTHERAPEUTIC SYSTEM

REFERENCE TO RELATED APPLICATIONS

This is a continuation of application Ser. No. 08/291,843, filed Aug. 17, 1994 (now abandoned), which in turn is a continuation-in-part of application Ser. No. 08/257,281, filed Jun. 9, 1994, abandoned, which in turn is a continuation-in-part of Ser. No. 08/082,610, filed Jun. 24, 1993 (now abandoned).

BACKGROUND OF THE INVENTION

This invention relates to an electromechanical system for the treatment of living tissues and/or cells by altering their interaction with their electro-dynamic and electrostatic environments. The invention also relates to a system for the modification of cellular and tissue growth, repair, maintenance, and general behavior by the application of encoded electrical information. More particularly, this invention provides for the application, by surgically non-invasive direct reactive coupling, of one or more electrical voltage and corresponding current signals conforming to highly specific electromagnetic signal patterns. The instant invention, accordingly, relates to the generalized area now known as electromagnetic medicine. That is, the use of electrical signals to modulate rates of in vivo biological growth and of repair processes.

This technology experience a relatively slow growth during the initial phase of its development which, generally, corresponded to the period of 1930 through 1975. The prior art reflective of work in this period is typified by French Patent No. 748,828 (1933) to Siemens which shows the use of a variable-width plate capacitor in an applicator head for use in electromagnetic therapy; and U.S. Pat. No. 2,130,758 (1938) to Rose which teaches the design of electrodes for use in a diathermy machine. Accordingly, diathermy, with its attendant property of penetrating thermal values to human tissue, represents the precursor of present day electromagnetic medicine.

Over time and, particularly, by about 1962, it was established that the effects of diathermy could be achieved by athermapeutic means, that is, means which, to the touch of a patient, did not appear to be transmitting heat or thermal values. Such patents are reflected in U.S. Pat. Nos. 3,043,310 (1964) and 3,181,535 (1965) both to Milinowski, directed to such athermapeutic treatment means. Accordingly, the extension of diathermy, into treatment means in which heating of the skin of the patient was no longer a limitation, enabled a much broader range of electromagnetic signal patterns to become potentially usable, at least experimentally, in the instant area. Use of an athermapeutic apparatus utilizing pulsed high frequency radiation in the range of 27 megacycles, and utilizing oscillations thereof of a sine waveform, is taught in said second Milinowski patent. Therein, Milinowski states that such an athermapeutic apparatus utilizing such pulsed high frequency radiation will produce greater beneficial results than EMF that can be applied without such pulsing of the waveform, particularly, in that heat tolerance is no longer a factor.

The technology of the use of pulsed electromagnetic fields (PRF) in the megahertz range within clinically usable apparatus first appeared in U.S. Pat. Nos. 3,270,746 (1966) and 3,329,149 (1967) both to Kendall, and further in U.S. Pat. No. 3,952,751 (1976) to Yarger, entitled High Performance Electrotherapeutic Apparatus. It is to be understood that the above is reflective of efforts in the prior art to employ bursts of EMF pulses in the megahertz range, this as opposed to other efforts in the prior art to employ bursts of pulses of electromagnetic waves which are in the kilohertz range or lower. It is, accordingly, to be understood that the instant invention does not relate to the area of low RF frequency electromagnetic therapy but, rather, is limited to the use of higher frequency waveforms and, more particularly, waveforms having frequencies in excess of one megahertz.

The use of most so-called low frequency EMF has been with relationship to applications of repair or healing of bone. As such, the EMF waveform and current orthopedic clinical use thereof involve relatively low frequency components and is of a very low power, inducing maximum electrical fields in the millivolts per centimeter (mV/cm) range at frequencies under five kilohertz. The origins of such a bone repair signal began with the early work of Becker, Yasuda, Brighton and Bassett; their work considered that an electrical pathway may constitute a means through which bone can adaptively respond to such an EMF input. This work was followed by a linear physicochemical approach taken by Pilla (one of the within inventors) who employed an electrochemical model of the cell membrane to predict a range of EMF waveform patterns for which bioeffects might be expected. This approach was based upon an assumption that the cell membrane was the most likely EMF target. This effort became one of finding the range of waveform parameters for which an induced electric field could couple to electrochemical, i.e., voltage-dependent kinetics, at the cellular surface. Extension of this linear model involved Lorentz force considerations which eventually led to the suggestion that the magnetic field along could be considered the dominant stimulus in EMF/PRF electrotherapy. These thoughts results in ion resonance and quantum theories that predicted benefits from combined AC and DC magnetic field effects at very low frequency ranges. This area of research is reflected in U.S. Pat. Nos. 4,105,017, 4,266,532 and 4,266,533, all to Ryaby, et al.

A second therapeutic EMF method to which the instant invention is more directly concerned, involves the use of a shortwave pulsed radio frequency (PRF) signals having a microsecond burst of megahertz sinusoidal waves with such bursts repeating between 0.01 and 1000 Hertz, and inducing a maximum electrical field in the volts-per-centimeter range at tissue level.

As above noted, a PRF signal derived from a 27 MHz continuous sine wave used for deep tissue healing is known in the prior art of diathermy and its above reference non-thermal successors thereto. A pulsed successor of the diathermy signal was originally reported by Giazberg as an electromagnetic field capable of eliciting a non-thermal biological effect in the treatment of infections. Since that original work, PRF therapeutic applications have been reported for the reduction of post-traumatic and post-operative pain and edema in soft tissues, wound healing, burn treatment, and nerve regeneration. The application of EMF for the resolution of traumatic edema has become increasingly used in recent years. Results to date using PRF in animal and clinical studies suggest that edema may be measurably reduced form such electro-physical stimulus.

Two general mechanisms have been proposed for the effect of PRF on edema. The first suggest that EMF affects sympathetic outflow, including vasoconstriction, which restricts movement of blood constituents from vascular to extravascular compartments at the injury site. The second proposes that the passage of electrical current through the tissue displaces the negatively charged plasma proteins found in the interstitium of traumatized tissue. This increase mobility, it is suggested, operates to accelerate protein uptake by the lymphatic capillaries, thereby increasing lymphatic flow which is an established mechanism for extracellular fluid uptake resultant from traumatic edema.

The within invention is based upon biophysical and animal studies which attribute the effect of cell-to-cell communication on the sensitivity of tissue structures to induced voltages and associated currents. These studies have established that prior art considerations of EMF dosimetry have not taken into account the dielectric properties of tissue structure (as opposed to the properties of isolated cells). The implications thereof are that a proper, i.e., an efficient reactive coupling of a PRF signal to tissue has not heretofore been effected in the art of record. This art, as is typified in the efforts of the last ten years relative to high frequency PRF, is reflected in U.S. Pat. Nos. 4,454,882 (1984) to Fellus, entitled Electrotherapeutic Apparatus; 4,674,482 (1987) to Waltonen, entitled Pulsed Electromagnetic Field Therapy Device; 4,998,532 (1990) to Griffith entitled Portable Electro-Therapy System; and 5,014,699 (1991) to Pollack et al, entitled Electromagnetic Method and Apparatus for Healing Living Tissue.

In recent years the clinical use of non-invasive PRF at radio frequencies has consisted of the use of pulse bursts, such pulses having a sinusoidal or other form, and at a frequency of 27.12 MHz, each such pulse burst typically exhibiting a width of sixty-five microseconds and containing a range of 1,100 to 10,000 pulses per burst, and with a pulse burst repetition rate in the range of 0.01 to 1,000 Hertz. At this high frequency, the burst duty cycle within the respective burst, in existing clinical equipment, has been in the range of one-half to four percent. A defining characteristic burst formed of such megahertz frequency pulses has been that of the configuration of the bi-polar amplitude envelope of the voltage of each pulse burst. This art is reflected in such clinical therapeutic devices as the SofPulse of Magnetic Resonance Therapeutics, Inc., Pompano Beach, Fla.

As noted above, a limitation in the art of record has been that efficient reactive coupling of the PRF signal to the tissue of interest has been difficult to accomplish. The instant invention addresses this problem by means of a system in which the impedance of the applicator head of the PRF apparatus is pre-set to an appropriate range of physiologic impedance and in which the power level of the PRF output of the pulse generating apparatus is continually monitored to thereby assure a closely regulated PRF signal input to the applicator head. This, in combination with tunable reactive means in the applicator head, enables delivery of PRF signal within the appropriate range of physiologic impedance. With such efficient reactive coupling to the tissue to be treated, various advantages of system efficiency and effectiveness of delivered PRF signals are accomplished.

SUMMARY OF THE INVENTION

The present invention sets forth a system for tissue-impedance matched pulsed radio frequency (PRF) electrotherapy in which said system includes a power supply; excitation means (i.e. generator means) for generating PRF signals of a selectable frequency, said means having an input from said power supply; means for power amplification of signals from said excitation means; means for controlling pulse width duration, pulse burst repetition rate, and amplitude of said PRF signals, said controlling means having an input from said power supply. Further provided are comparator means for continually comparing the amplitude of said PRF signals outputted from said amplification means to a reference value therefor, said means including feedback means responsive to difference information between the compared signals and said reference value, said difference information being inputted to said controlling means for adjustment of amplitude and impedance of said PRF signals from said excitation means, said comparator means including an output of power and impedance compensated PRF signals. The system yet further includes a variable reactance athermapeutic applicator having, as a coaxial cable input thereto, said power and impedance compensated PRF signals being outputted from said comparator means, said applicator including a treatment surface having an effective physiologic impedance in the range of 0.10 to 0.15 ohms.

It is an object of the present invention to provide a means of PRF electrotherapy having improved reactive coupling to the tissue to be treated.

It is another object to provide a system of the above type having improved tissue impedance matching to the tissue to be treated.

It is a further object to provide a system having, as an aspect thereof, an athermapeutic applicator head including a tunable reactance.

It is a yet further object of the invention to provide a system for use with PRF electrotherapy having particular utility in the treatment of both soft and hard tissue.

It is another object to provide a system usable for electrotherapeutic treatment having a broad band, high spectral density electrical field and associated PRF current signal.

it is a still further object of the invention to provide a system to enable the practice of electrotherapeutic methods in which amplitude modulation of a pulse burst envelope of the electromagnetic signal will induce coupling to a maximum number of relevant dielectric pathways within the cells of the tissue of interest.

It is a further object to provide an electrotherapeutic system having such enhanced portability and efficiency of operation as to provide beneficial effects to living cells and tissue by the modulation of voltage sensitive regulatory processes of cell membranes and at junctional interfaces between cells.

It is a yet further object of the invention to provide an electromagnetic system of the above type in which system operation can proceed at reduced power levels, as compared to those of related methods known in electromedicine, with attendant benefits of safety, economics, portability and reduced electromagnetic interference.

The above and yet other objects and advantages of the present invention will become apparent from the hereinafter set forth Brief Description of the Drawings, Detailed Description of the Invention, and claims appended herewith.

DETAILED DESCRIPTION OF THE INVENTION

With reference to the perspective view of FIG. 1 there is shown, to the left thereof, a PRF generator 10, more fully described below, and a variable reactance athermapeutic applicator head 12 by which PRF energy is applied to the patient. Said head 12 receives PRF energy from generator 10 through coaxial cable 14 while the alternating current (AC) input to the generator is obtained through electrical cord 16. As may be seen upon the face of generator 10, there are provided three dials which, more particularly, include power control dial 18, pulse repetition rate (PPS) dial 20 and treatment duration dial 22. Also shown on the face of generator 10 is display counter 24 which provides, to the user, real time information respecting the time that the generator has been in operation during a given treatment session. Further shown on the face of generator 10 is start/stop momentary switch 26.

At the back of generator 10 are cooling fins 28 as well as interfaces with said co-axial cable 14 and A/C power input cord 16.

Figure 1:
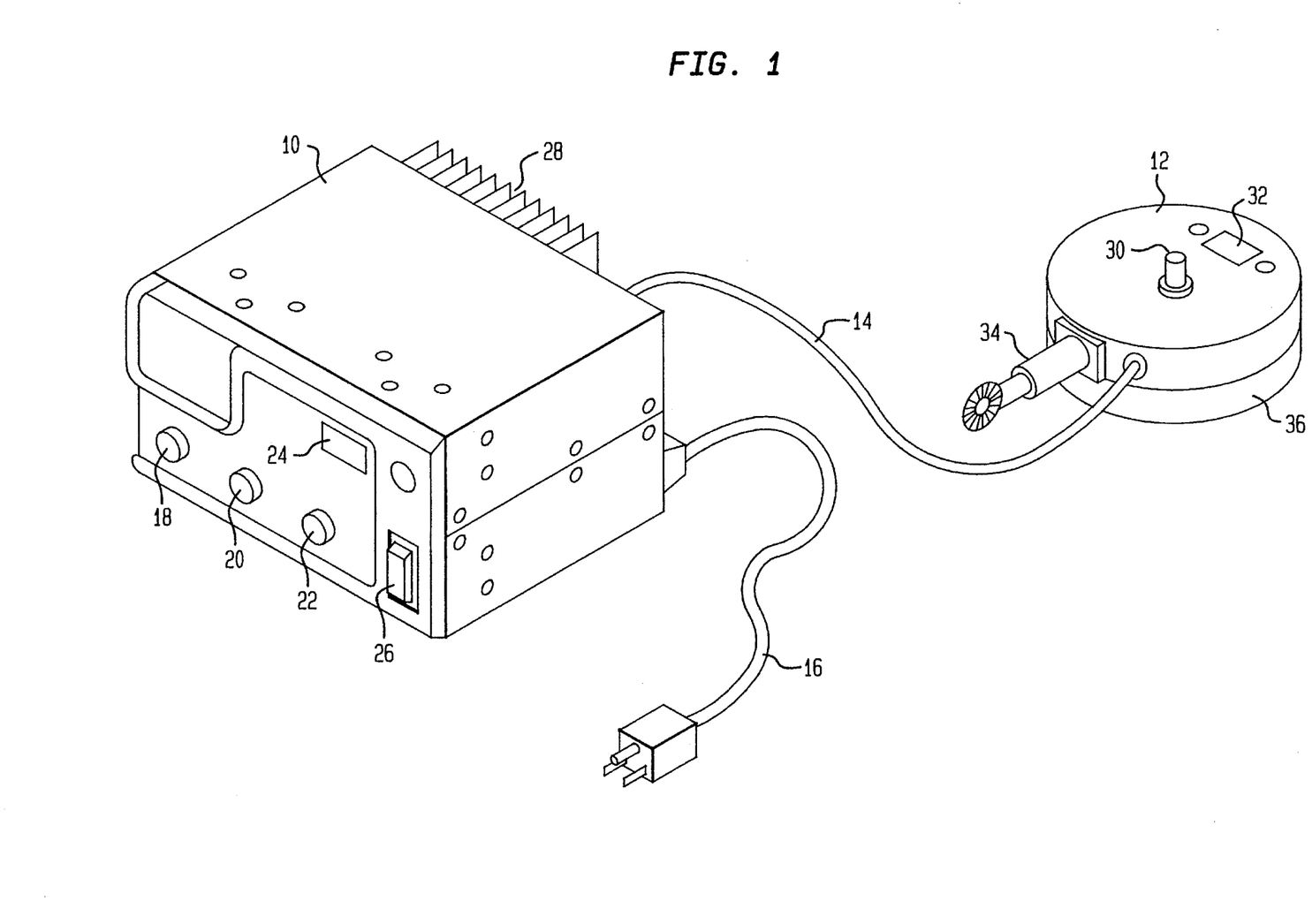
FIG. 1 is a perspective view of PRF-generator and applicator-head components of an electrotherapeutic system of the invention.

With further reference to applicator head 12 there is, in the view of FIG. 1, shown thereon a variable-reactance feature in the form of capacitance tuning means 30 and power meter 32 (both more fully described below) as well as handle 34 and a disc element 36 providing a patient treatment surface.

Figure 2:
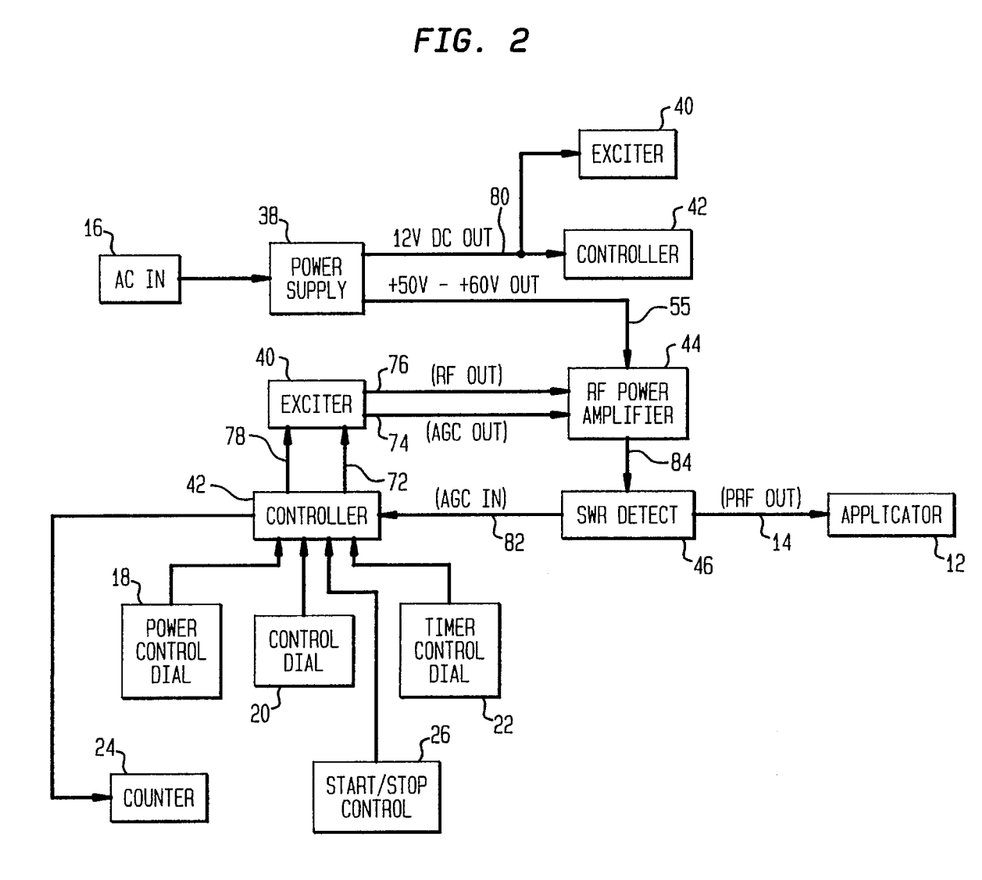
FIG. 2 is a block diagram of the system of FIG. 1.

With reference to the system block diagram of FIG. 2, the primary subsystems of the inventive system may be seen to include a power supply 38, a PRF exciter 40 (sometimes referred to as a generator), a system controller 42, an RF power amplifier 44, and a standing wave ratio (SWR) detector circuit 46.

Figure 3A:
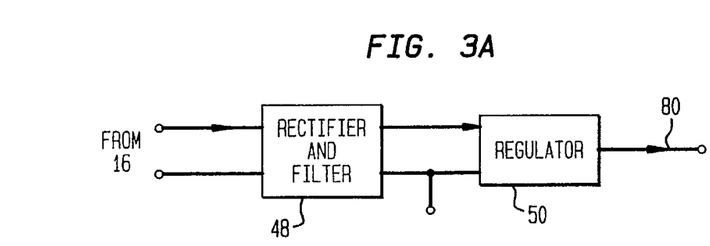
FIG. 3A is a block diagram of a first power supply in the system of FIG. 1.

As may be noted, the function of power supply 38 is to provide a first DC output 80 in the range of 12 to 15 volts to the exciter 40 and controller 42 and to provide a second DC output 55 in the range of 50 to 60 volts to the power amplifier 44. The manner in which this is accomplished is more particularly shown in the views of FIGS. 3A and 3B. More particularly, in FIG. 3A a rectifier and filter 48, together with a regulator 50, converts the A/C input 16 into the desired first D/C output 80, in the range of 12 to 15 volts DC ($V_{dc}$). And in FIG. 3B, a rectifier and filter 52, together with a voltage limiter 54, converts the A/C input 16 into the desired second DC output 55, in the range of 48 to 60 volts DC ($V_{dc}$), for use by power amplifier 44.

Figure 3B:
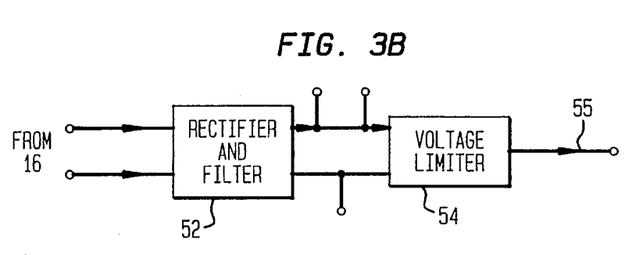
FIG. 3B is a block diagram of another power supplying the system of FIG. 1.

It is further noted that the power supply 38 utilizes a UL/CSA qualified low leakage transformer (not shown) to supply the power voltages to the internal circuitry. In the event of a short circuit, the primary of the transformer is protected with a fuse located inside the unit next to the transformer. The transformer's secondary voltages are, in said rectifier/filters 48/52, rectified and filtered by full-wave capacitative input filters. It is further noted that in the context of the two output voltages 80 and 55 shown in FIGS. 3A and 3B respectively, a current of about one ampere can be supplied. The regulator that offers current and thermal protection, while the 50 Vdc output 80 of FIG. 3B is has a voltage upper limit, regulated at 60 volts using a discrete regulator, this being the function of voltage limiter 54.

With further reference to the system block diagram of FIG. 2, the instant inventive system may be seen to include exciter means 40, the function of which is to generate PRF signals of a selectable megahertz frequency, typically in the range of one-to-100 megahertz but, preferably, at the FCC-approved biotherapeutic (medical-diathermy) frequency of 27 megahertz. Pulse-burst-width control, e.g., a pulse burst width of 65 microseconds, is applied to exciter 40 through the digital logic of controller 42 (more fully described below). Similarly, the power amplitude of the PRF output of exciter 40 is controlled by an automatic gain control (AGC) circuit in controller 42 in combination with the SWR detection circuit 46, as are more fully set forth below. That is, through the adjustment of dials 18, 20 and 22, controller 42 operates as a means for control of pulse width duration, pulse burst repetition rate, and power amplitude of the PRF signals produced by exciter 40 and furnished to power amplifier 44.

Figure 4:
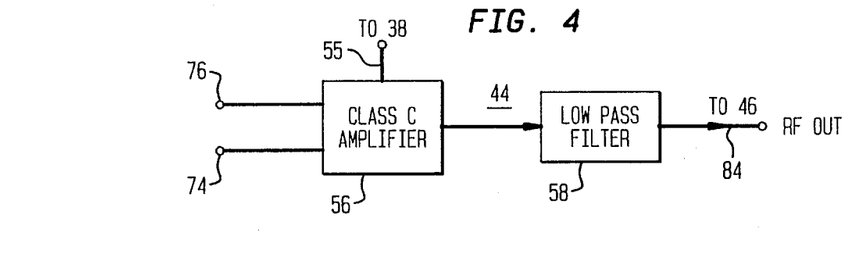
FIG. 4 is a block diagram of a RF power amplifier in the system of FIG. 2.

Power amplifier 44 is more fully shown in the subsystem block diagram of FIG. 4 wherein it may be seen that the power amplifier comprises the combination of a Class C amplifier 56 and a low-pass filter 58. More particularly, power amplifier 44 employs two high voltage MRF-150 Mosfet's (FETs) in push-pull relationship at 60 Vdc maximum voltage. These FETs operate Class B through C, depending upon the desired output power level. Gate voltage is controlled by a power output control loop. At higher output power levels, a minimum amount of forward bias is applied to the FETs to maintain the desired shape of the pulse-burst envelope and to increase gain at the power amplifier stage. Low pass filter 58 is a five pole Chebyshev filter used for harmonic reduction. This filter operates to reduce harmonic energy to negligible levels.

Further shown in FIG. 4 is AGC input 74 and RF input 76 to the amplifier 56, as is RF output 84 to the SWR detector circuit.

Figure 5:
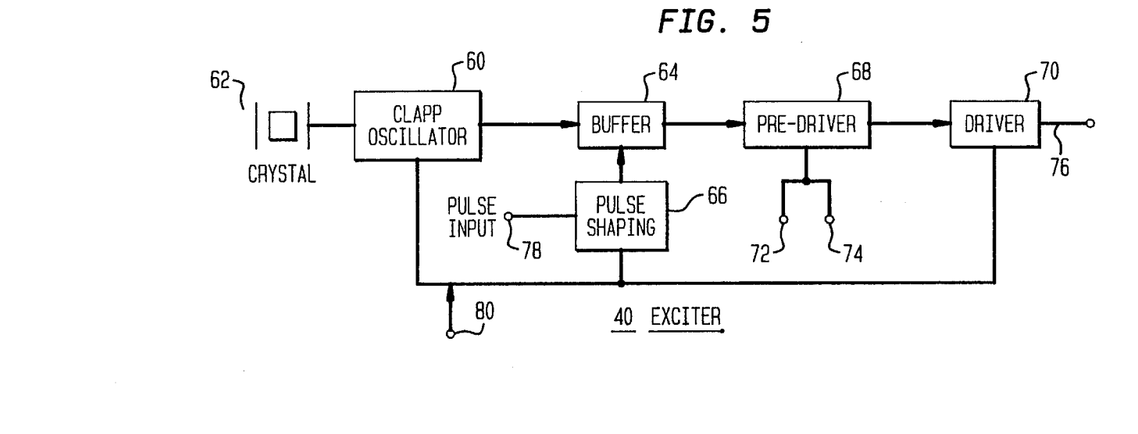
FIG. 5 is a block diagram of the exciter assembly in the PRF generator of FIG. 2.

With further reference to the subsystem of exciter 40, the same is shown in block diagram format in the view of FIG. 5. It may, with reference thereto be noted that said RF exciter uses a fundamental frequency clamp oscillator 60 which is controlled by a crystal 62 that is located within exciter 40. The following state shown in FIG. 5, is a Class AB keyed buffer 64 that isolates, amplifies and chops the oscillator pulses into a square-envelope RF wave of approximately 65 microsecond duration. The output of this stage exhibits less than one microsecond of rise and fall time. Buffer 64 is switched on and off by a pulse-shaping switch 66 (having pulse input 78 from controller 42) which may comprise a series NPN transistor which sources the voltage to stage 64 while a shunt PNP transistor discharges buffer 64 to supply voltage at the end of each pulse.

The signal output of buffer 64 is fed into a pre-drive 68 which operates from a variable voltage source that is a part of a power output control loop. Pre-driver 68 obtains input 72 from controller 42, and provides AGC output 74 to RF amplifier 44 (see FIG. 2). Said pre-driver 68 is followed by a Class C driver stage 70 that operates at a constant 12 Vdc, and which provides RF output 76, of 27.12 MHz at a 5 watt maximum, to amplifier 44.

Figure 6:
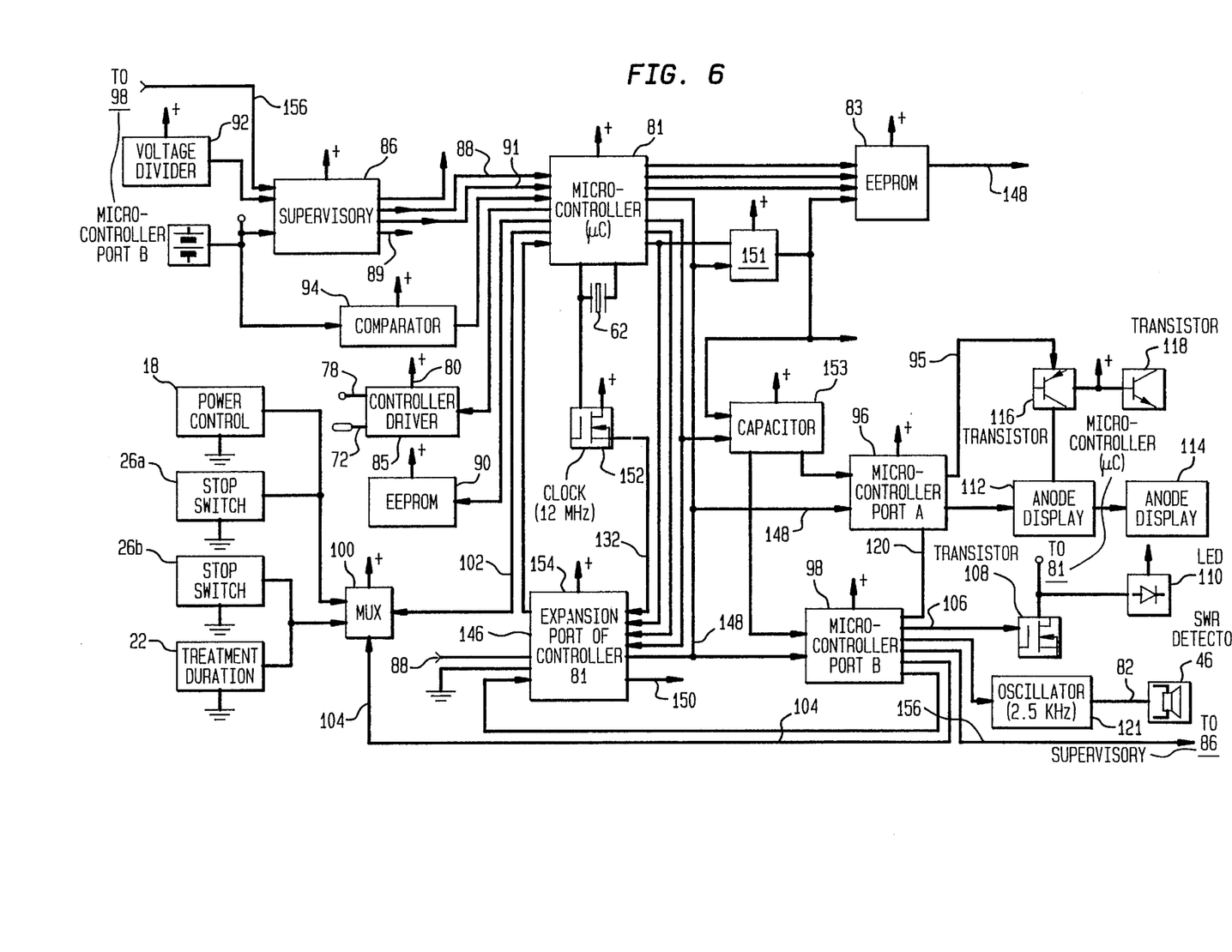
FIG. 6 is a block diagram of the controller assembly in FIG. 2.

With reference to FIG. 6 there is shown, in block diagram sub-system view, controller 42, also alternately referred to below as control board 42.

Controller 42 provides the necessary timing, user interface, and control signals to operate the present inventive system for tissue-impedance matched PRF electrotherapy.

In a preferred embodiment, controller 42 uses a Type 80C32 μC microcontroller 81 running at 12 megahertz. Furthermore, a 150-nanosecond, 8 kb, 8-bit EPROM is used. In view of the actual memory requirement of the system, that is, about one kilobyte, such memory sizing is adequate for future expansion.

The power input 80 from power supply 38 is inputted to controller driver 85 for use by the rest of the controller 42. A regulator (not shown) down-converts this voltage to the 5 Vdc required by the digital electronics of controller 42.

The microcontroller 81 is supervised by a supervisory circuit 86 of the 691 type. This provides a 200-msec reset pulse 88 after a power-up operation has been initiated by actuating start switch button 26a (FIG. 6).

Software failures are prevented by using watchdog signals 89 from supervisory circuit 86. A WDT port B of the supervisory 86 changes state approximately every 1.2 seconds. If this change does not occur, an operating reset operation will be initiated, via line 88.

The various necessary operating parameters of this system are stored in an internal RAM of microcontroller 81 or, alternatively and preferably, in a serial programmable EPROM 90 of the 27CO4 type. Therefore, it is generally not necessary to use the UC RAM back-up of microcontroller 81 or the battery fault signal 91 of supervisory circuitry 86.

After a reset 88 occurs the memory of the EPROM 90 is downloaded into the internal RAM of microcontroller 81, which will be understood to have retained all the parameters from the last power-down. The retained parameters include inter alia the time remaining from the time selected by treatment duration dial 22 (with a precision in the order of microseconds) and the pulse per second (PPS) setting accomplished by dial 22 (see FIG. 1).

A serial IIC protocol is employed for communication to the EPROM 90.

After power-down, microcontroller 81 initiates a non-maskable interrupt subroutine which prevents loss of stored operating parameters. An internal reference of 1.25 volts within supervisory 86, in combination with a voltage divider 92 (see upper right hand corner of FIG. 6) and a voltage comparator 94 causes a power-down signal to be generated. Information is preferably stored in tents of milliseconds before the five-volt power supply of the supervisory circuit 86 reaches a critical level.

Initial display blinking level on LED 24 on the face of the generator (see FIG. 1) is effected by enabling or disabling the output 95 of a display-control circuit governing a port A of a microcontroller 96, in response to a display-enabling signal in line 129 from a port B of a signal-generating circuit 98 controlled by microcontroller 81. The instantaneous status of settings of time dial 22, PPS dial 20, power setting 18 and start and stop switches 26a and 26b respectively are tested approximately every 50 milliseconds by microcontroller 81. A multiplexer 100 selects either the PPS dial 20 and the start switch 26a, or the time setting 22 and the stop switch 26b, for input 102 to microcontroller. Control of multiplexer 100 is accomplished through a switch-select signal 104 from port B of signal-generating circuit 98.

The positions of setting 22 and switch 26a are decoded in inverted binary logic to simplify programming. When the generator 10 is activated by the start switch 26a, a power output 106 of port B of signal-generating circuit 98 is enabled, thereby turning-on transistor 108 and enabling inboard LED 110 and a timer counter within microcontroller 81. Two common-anode displays 112 and 114, which are in communication with port. A of microcontroller 96 indicate time status at counter 24. That is, port A controls the segment activation and selection of displays 112 and 114 and of complementary transistors 116 and 118. These displays are disabled by setting the display-enable signal 120 to port B at a sufficiently high level.

A piezoelectric buzzer and a 2.5 kilohertz oscillator 121 (see lower right corner of FIG. 6) serve as an alert indicator. Said buzzer is enabled by a buzzer-enable signal 122 from said port. B 98 of signal-generating circuit.

Power level rotary switch 18 (see FIGS. 1 and 7) enables selection of any one of six pre-adjusted voltage references as input (labelled "Power Ref.") to comparator 142. Multi-turn reference potentiometers 126, 128, 130, 132, 134 and 136 are accessible from a test connector. Comparator 142 will trip (actuate) to a low value when the voltage at point 138 (see FIG. 7) indicates that the actual power level is larger than that of a selected reference. As may be noted, a driver 140 is used with phase lag (in order to stabilize the loop for any low power setting) which follows comparator 142 within the oscillator 121 (FIG. 6). Output 72 of driver 140 functions as an automatic gain control (AFC) input to the pre-driver 68 of exciter 40 (see FIG. 5).

Figure 7:
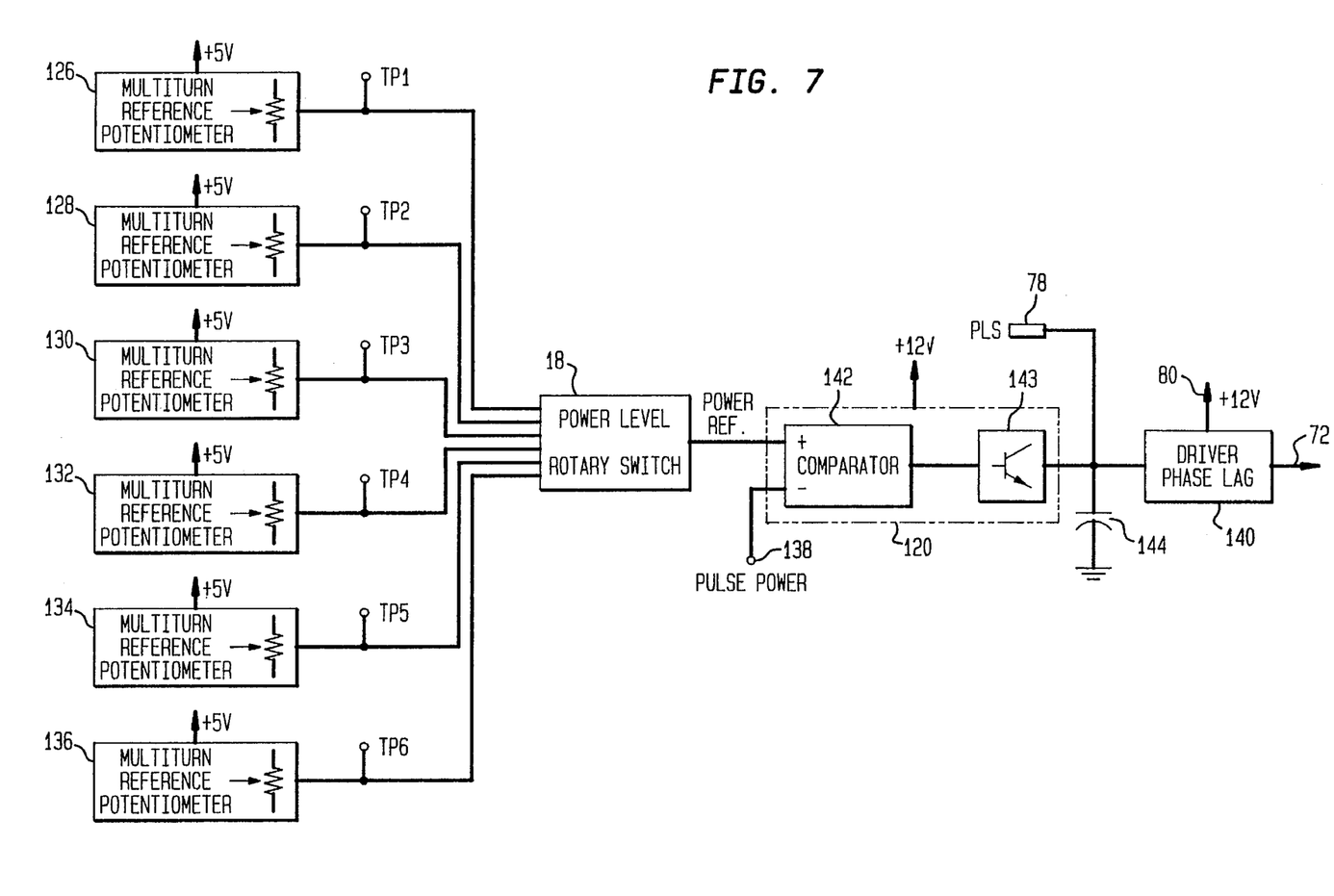
FIG. 7 is a block diagram to show provision for automatic gain control (AGC) in the controller of FIG. 6.

Driver 140 is activated only in the presence of pulses at point 138 (see FIG. 7). This is due to the open collector output 143 of comparator 142. That is, if no pulses are present, the comparator remains low, and a capacitor 144 (see FIG. 7) will initiate or continue its discharge. The "on" transition of the generator is thereby smoothed, since capacitor 144 is loaded gradually through a resistor within oscillator 121 (FIG. 6) as soon as the actuating 65-microsecond pulse train appears at input 138 to comparator 142. As the cadence set by the selection at PPS dial 20 and while the power is on, microcontroller 81 will be set low for 65 microseconds. The driver 85 (see FIG. 6) then changes the polarity and the voltage level of its pulse output. A transistor then causes the fall time of the pulses to become shorter. The pulse output 78 then becomes the pulse input of the pulse-shaping circuit 66 of exciter 40 (see FIG. 5).

It is noted that an expansion port 146 serves as an expansion port for the entire controller. Among the more important pin positions of expansion port 146 are data bus 148, address bus 150 and 5 Vdc power pin 154. As may be noted, expansion port 146 is also in communication with microcontroller 81 through numerous additional pin locations which are shown at the upper left and upper right of the expansion port. A provided a twelve megahertz system clock 152 is common to both the microcontroller and the expansion port.

Further shown in FIG. 6 is twelve megahertz crystal 62 which provides the time reference for system clock 152 and for exciter 40 above described with reference to FIG. 5.

Generation of the 65-microsecond pulse train is realized by using the Timer ZERO of the controller in Mode 2 and pre-setting the reference to be loaded into the microcontroller 81. This provides a 100-microsecond unit of count to the system. The number of interrupts is then compared to the value of the selected pulses per second from the PPS cadence, and a pulse is thereupon generated if both match.

With reference to port B of signal-generator circuit 98 (see FIG. 6), the watchdog signal at 156 is refreshed by a watchdog-refreshing subroutine that is included in the subroutine that manages the displays 112 and 114. The watchdog-refreshing subroutine causes the supervisory circuit 86 to generate its reset pulse 88 whenever system timing is within 100 microseconds of the 1.2 seconds limit which is the default-trigger time for supervisory circuit 86.

With respect to back-up of data, the parameters of microcontroller 81 are stored in EPROM 90. Several subroutines perform a IIC two-wire serial transmission protocol required for correct operation of EPROM 90. At power-on, these EPROM-90 parameters are recalled. A power-down transition generates a non-maskable interrupt that writes the current device parameters into the EPROM 90.

Figure 8:
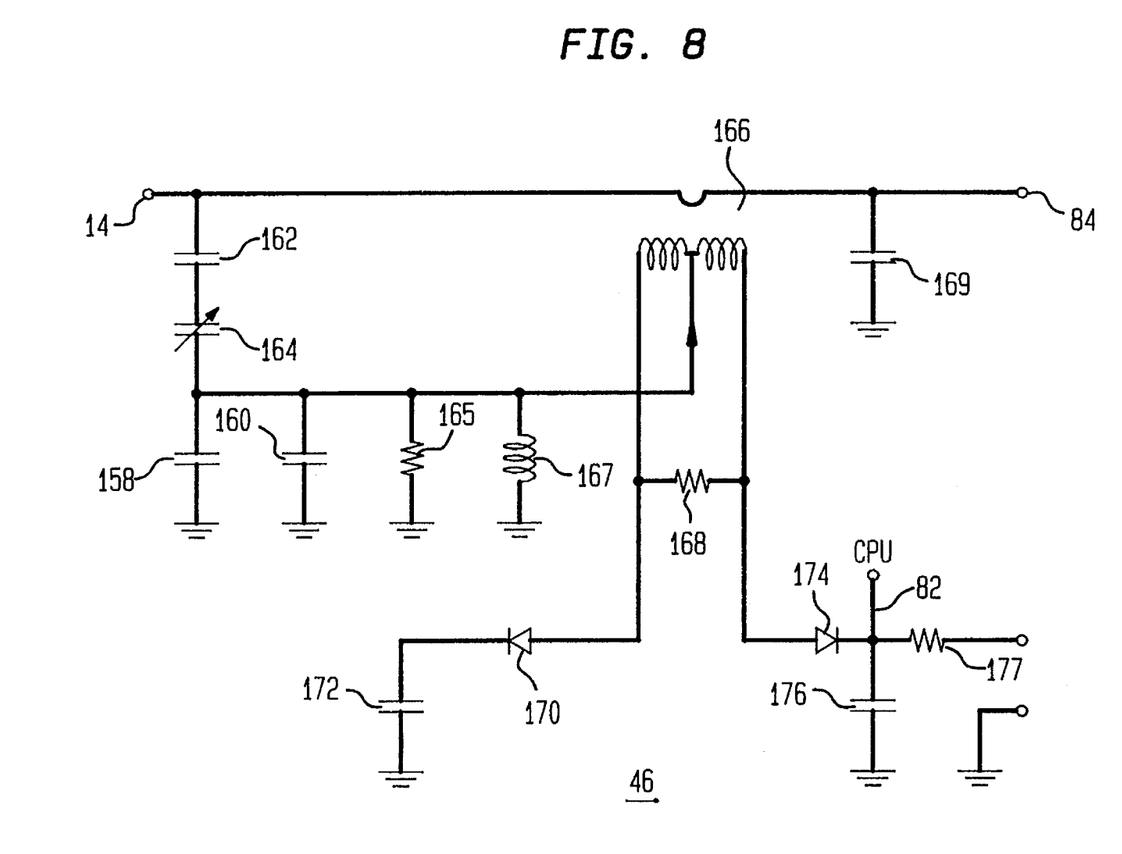
FIG. 8 is a block diagram of standing-wave-ratio (SWR) detection circuitry in the system of FIG. 2.

The standing-wave ratio (SWR) detection circuit 46 of FIG. 8 has an input connection 84 from power amplifier 44 (FIG. 2), as well as an output connection 14 to applicator 12 (FIG. 1) and an output connection 82 to controller 42 (FIG. 2).

The function of the SWR circuit 46 is to compare current phase and ratios in the transmission cable 14 that feeds the applicator 12 to thereby provide a means for continually comparing the amplitude, and thereby impedance, of PRF signals outputted from amplifier 44, the comparison being made to a reference value therefor. Such means, as is set forth below, includes feedback means responsive to difference information between the compared PRF signals and said reference value. This difference information is inputted to controller 42 at input 82 to continually effect adjustments of the amplitude of the PRF signals from exciter 40 and to continually monitor the output of power amplifier 44, to thereby provide to co-axial cable 14 power and impedance compensated PRF signals for the applicator 12.

The above comparing function is accomplished through a form of a non-directional voltage sampling (see FIG. 8) which is accomplished by a voltage divider including a 150 pF capacitor 158, a 150 pF capacitor 160, a 33 pF capacitor 162, and a 3–14 pF variable capacitor 164. The current to cable 14 is sampled with a current transformer assembly which includes transformer 166, a 1000 μH inductor 167 and a resistor 168. Said current transformer provides two 180-degree directionally sensitive phase-shifted outputs. One of the current transformer outputs, namely, the output at diode 170 and capacitor 172, provides a vector subtraction of the capacitive-voltage-divider output and one of the current-transformer outputs. The other current-transformer output provides a vector sum of the capacitive-voltage-divider output and of the current transformer voltage outputs, this output occurring across diode 174 and capacitor 176.

Variable capacitor 164 adjusts the capacitive-voltage-divider output until it matches the output voltage from the current transformer 166 with a zero phase shift 50-ohm resistive RF load, that is employed for calibration purposes, on the generator output. Such matching to a resistive RF load accomplishes an effective matching, within 0.10 to 0.15 ohms/sq.cm. of tissue, to the physiological impedance of the tissue, to of the patient to be treated. As a consequence, optimal reactive coupling between the PRF output of the present system and the tissue to be treated by the applicator 12 is accomplished.

With further reference to the SWR circuit of FIG. 8, it is noted when the RF voltage of the capacitive divider exactly matches the voltage across one-half of the current transformer, the voltage at detector diode 170 and the capacitor 172 will be zero. The voltages across the diode 174 and the capacitor 176 will, as above noted, appear as the vector sum of the two voltages. If any reactance appears in the load, or if the resistance of the load is no longer at the desired 50 ohms impedance, output power to cable 14 will be automatically reduced. Such automatic reduction achieves a precise degree of power regulation, thereby maintaining the voltage level of the PRF pulse train supplied to applicator 12, within the desired therapeutic range.

Figure 9A:
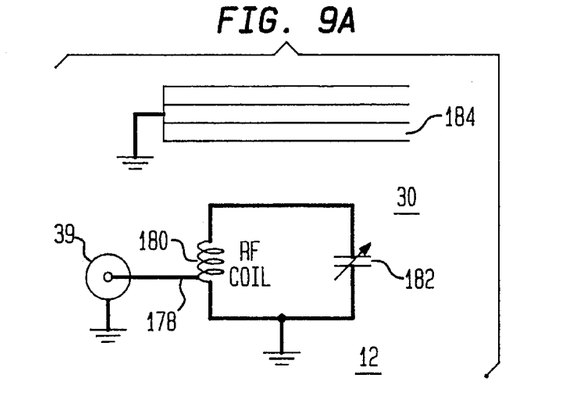
FIG. 9A is an electrical schematic of components in the applicator head of FIG. 1.
Figure 9B:
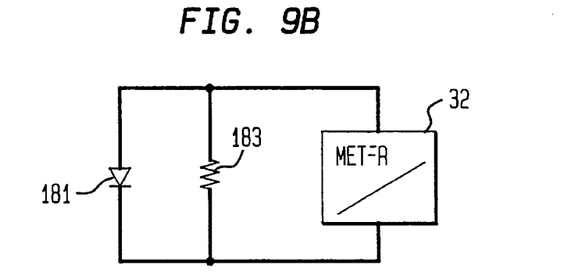
FIG. 9B is a schematic diagram of a power meter associated with the applicator head of FIG. 1.
Figure 10:
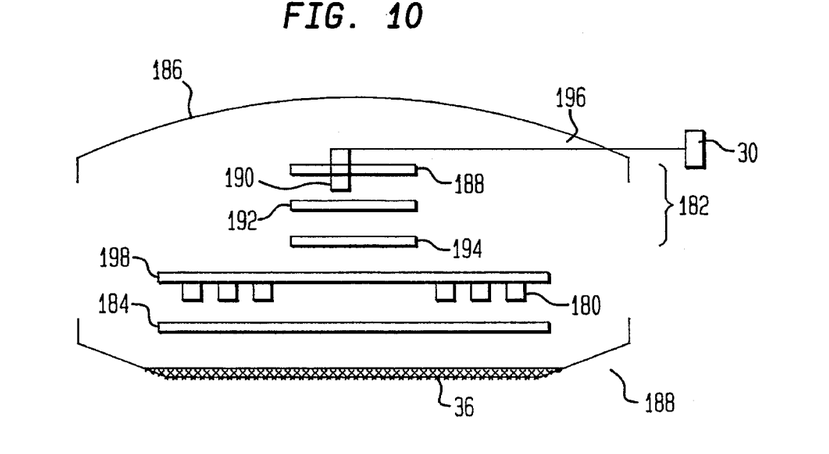
FIG. 10 is a simplified cross-sectional view of the applicator head of FIG. 1, taken in a diametral plane which includes the central axis of the applicator head.
Figure 11:
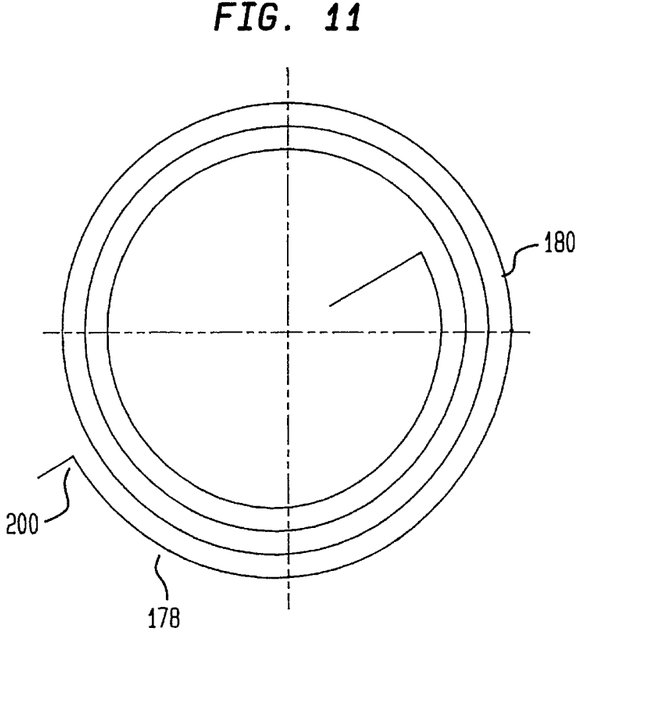
FIG. 11 is a plan view of the RF coil (180) shown in FIGS. 9A and 10.
Figure 12:
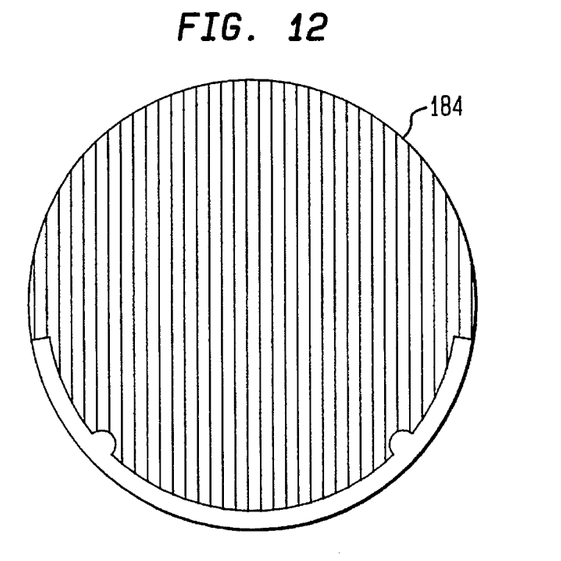
FIG. 12 is a plan view of a Faraday shield (184) shown in FIGS. 9A and 10.

FIGS. 9 through 12 illustrate electromechanical elements of the variable-reactance athermapeutic applicator 12. In FIG. 9A, coaxial cable 14 to applicator 12 carries power and impedance-compensated PRF signals from the SWR-detection circuit (FIG. 2). These power and impedance-compensated signals are inputted, via line 178 to RF coil 180, which is also shown in FIGS. 10 and 11. As is more fully described below, the reactance and power level of the output of RF coil 180 is controlled through a variable capacitor 182 having external control 30 which is also shown in FIGS. 1 and 10. Shown above coil 180 and variable capacitor 182 in FIG. 9A is a Faraday shield 184 which is also shown in FIGS. 10 and 12.

FIG. 9B shows power meter 32 (FIG. 1) which, through the positioning of diode 181 and resistor 183 within the field of coil 180, enables measurement of power delivered to the applicator.

FIG. 10 shows that the applicator 128 of the invention includes a housing 36 (FIG. 1) having an upper surface 186 and a lower (i.e., patient-treatment) surface 188. Typically, the housing 36 is about nine inches in diameter (i.e., for the horizontal extent of FIG. 10) and about six inches deep (i.e., the vertical extent of FIG. 10). The upper and lower ports 186, 188 of the applicator housing will be understood to be secured to each other, in order to enclose the operative applicator components therewithin.

These operative components are, starting at top housing surface 186, in succession, a rectangular plate 188 integrally fixed to a bushing 190 which carries plate 188 externally controlled by tuning means 30. Rotation of tuning means 30 displaces capacitor plate 192 such that it will tilt relative to a fixed capacitor plate 194 to thereby define variable capacitor 182. Any one of a number of mechanical configurations may be employed to effect changes in orientation or attitude of movable capacitor plate 192 relative to fixed capacitor plate 194, it being indicated that in FIG. 10, the mechanical communication between tuning means 30 and bushing 190 is a spring plate 196.

FIG. 10 shows, beneath variable capacitor 182, a nylon support 198 for RF coil 180 (see also FIG. 11), it being noted that RF coil 180 has an input connection 178 for reception of the PRF signal. FIG. 10 also shows, beneath RF coil 180, the Faraday shield 184 and, therebeneath, the patient-treatment surface of housing 36, which illustratively has an area of about 120 square centimeters.

RF coil 180 and variable capacitor 182 constitute a resonant (RLC) tank circuit through which RF currents circulate. Approximately half of the circulating current flows through the Faraday shield 184 to the inside of the applicator housing and it loops therefrom through the fixed capacitor plate 194. The RLC tank circuit focuses the PRF signals through Faraday shield 184 and the patient-treatment surface of housing 36.

A further significant aspect of the RLC circuit that is defined by the combination of RF coil 180 and variable capacitor 182 is that of assuring constant power and impedance of the PRF RF current delivered through treatment surface of housing 36 in order to maintain an effective physiological impedance match with the impedance of the tissue to be treated, thereby maximizing reactive coupling between the device and the operative dielectric cellular pathways and channels to be treated.

With further reference to FIG. 11, it should be noted that position 200, at which input 178 is provided, may be adjusted as a further means of adjusting the impedance match of the applicator to tissue to be treated.

FIGS. 1 and 9B show meter 32, situated within upper housing 186 of applicator 12. Meter 32 displays electromagnetic field strength within the housing. It has been determined that a given level of field strength will assure performance with minimal distortion of the SWR current level inputted through coaxial cable 14 and, thereby, will provide further assurance of delivery of PRF signals through the lower treatment surface of housing 36 which is in the range of 0.10 to 0.15 ohm/sq. cm. or 25 to 75 ohms and, optimally it has been found at 50 ohms, this constituting the optimal physiologic impedance with which the inventors have been found to exist in human tissue given a treatment surface of housing 36 having an area of about 120 sq. cm. That is, where if the treatment surface of housing 36 is smaller, a lesser impedance will constitute a physiological matching impedance; and, correspondingly, if the diameter of treatment surface of housing 36 is greater, a greater impedance will constitute the effective physiological impedance.

FIG. 12 shows a preferred embodiment of Faraday shield 184 which, it has been found, can be constructed through use of 1,440 traces of copper foil, wherein the traces are of 0.025-inch width. The same may be accomplished with a printed circuit wafer having a diameter of about eight inches.

It is, thereby, to be appreciated that the above described applicator head structure provides a simple, relatively low cost design by which the level of PRF fields may be carefully adjusted and in which, through the use of Faraday shield 184, the applicator is rendered essentially free of stray electromagnetic field.

It is noted that the range of capacitance achievable by variable capacitor 182 is that of 2.5 pF to 6.5 pF, this occurring as the applicator is used across a range of 25 to 30 megaHertz.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth in the claims appended herewith.

Having thus described our invention what we claim as new, useful and non-obvious and, accordingly, secure by Letters Patent of the United States is:

1. A system for tissue-impedance matched pulsed radio frequency (PRF) electrotherapy, the system comprising:

(a) a power supply;

(b) means for generating PRF signals of selected carrier frequency and of a selectable pulse-repetition rate (PPS), said means having an input from said power supply;

(c) means for power amplification of PRF signals from said generating means;

(d) said generating means including means for controlling pulse-width duration, pulse-repetition rate, and amplitude of said PRF signals, said controlling means having an input from said power supply;

(e) comparator means, including a standing-wave-ratio detection circuit (SWR) having a predetermined value of reference-voltage amplitude and phase of an RF signal across an impedance in a range of 25 to 75 ohms, for continually comparing the voltage amplitude and phase of said PRF signals outputted from said amplification means to the reference amplitude value, said SWR circuit producing a ratio signal representative of said comparison, said comparator means including feedback means responsive to said ratio signal for inputting said ratio signal to said controlling means for adjustment of the amplitude and phase of said PRF signals from said generating means, said comparator means providing an output of power and impedance compensated PRF signals; and (f) a variable reactance athermapeutic applicator having, as its input thereto, the compensated PRF signals outputted from said comparator means, for inducing said compensated PRF signals into tissue to be treated, said applicator comprising first and second spaced parallel capacitor plates; a magnetic coil wound in a plane parallel to and electrically connected to said capacitor plates; an RF shield positioned parallel to said coil and on a side of said coil opposite from said capacitor plates; and control means for varying the space between said capacitor plates.

2. The system as recited in claim 1, in which said applicator comprises:

first and second capacitor plates proximally spaced in substantially parallel relationship thereto;

a magnetic coil wound in a plane parallel to said capacitor plates;

an RF shield positioned parallel to said coil and on a side of said coil opposite from said first and second capacitor plates; and control means for varying the distance between said first and second capacitor plates.

3. The system as recited in claim 1, in which said applicator further includes a housing for containment of said plates, said coil, said shield and said control means.

4. The system as recited in claim 3, in which said first capacitor plate is movable relative to said housing and in which said second capacitor plate is fixed relative to said housing, and in which said control means comprises a spring plate fixed to said housing, said plate having a screw hole, and a screw mechanism in threaded engagement to said spring plate via the screwhole, and means for selectively operating said screw mechanism to displace said first capacitor plate to vary the space between said plates.

5. The system as recited in claim 3, in which said first capacitor plate is moveable relative to said housing and in which said second capacitor plate is fixed relative thereto.

6. The system as recited in claim 5 including a spring plate attached to said housing in which said first capacitor plate integrally extends from said spring plate.

7. The system as recited in claim 6, further comprising:

a bushing plate affixed to said upper housing plate, said busing plate having a hole therein;

a screw member disposed in said hole and in communication with said first capacitor plate;

control means for controllably turning said screw to change the distance between said first and second capacitor plates.

8. The system as recited in claim 1, in which said RF shield comprises a planar member having an array of electrically grounded linear foil traces thereon.

9. The system as recited in claim 8, in which said planar member comprises a copper wafer.

10. The system as recited in claim 2, in which said comparing means includes phase comparison means between said PRF signal and said reference value therefore.

11. A system for tissue-impedance matched pulsed radio frequency (PRF) electrotherapy, the system comprising:

a) a power supply;
   b) means for generating PRF signals of selected carrier frequency and of a selectable pulse repetition rate (PPS), said means having an input from said power supply;
   c) means for power amplification of PRF signals from said generating means;
   d) said generating means including means for controlling pulse width duration, pulse repetition rate and amplitude of said PRF signals, said controlling means having an input from said power supply;
   e) comparator means including a standing wave ratio detection (SWR) circuit having a predetermined value of reference voltage amplitude and phase of an RF signal across an impedance in the range of 25 to 75 ohms, for continually comparing the voltage amplitude and phase of said PRF signals outputted from said amplification means to the reference amplitude value, said SWR circuit producing a ration signal representative of said comparison, said comparator means including feedback means for adjustment of the amplitude and phase of said PRF signals from said generating means, said comparator means providing an output of power and impedance compensated PRF signals; and
   f) a variable reactance athermapeutic applicator having, as its input thereto, the compensated PRF signals outputted from said comparator means, for inducing said compensated PRF signals into tissue to be treated.

* * * * *